United States Patent [19] [11] Patent Number: 4,589,869
Wernborg [45] Date of Patent: May 20, 1986

[54] SUCTION DEVICE AND A METHOD OF MANUFACTURING THE SAME

[75] Inventor: Rune Wernborg, Kållered, Sweden

[73] Assignee: Mediplast AB, Solna, Sweden

[21] Appl. No.: 552,133

[22] PCT Filed: Feb. 23, 1983

[86] PCT No.: PCT/SE83/00061
§ 371 Date: Oct. 13, 1983
§ 102(e) Date: Oct. 13, 1983

[87] PCT Pub. No.: WO83/02900
PCT Pub. Date: Sep. 1, 1983

[30] Foreign Application Priority Data
Feb. 24, 1982 [SE] Sweden ............................. 8201137

[51] Int. Cl.⁴ ............................................. A61M 1/00
[52] U.S. Cl. .................................... 604/119; 604/247; 604/902

[58] Field of Search .............. 604/118, 119, 129, 153, 604/247, 902; 128/205.19, 207.14, 910; 433/92; 285/110; 137/526, 854, 855

[56] References Cited
U.S. PATENT DOCUMENTS
2,347,988 5/1944 Burke .................................. 137/256
3,419,009 12/1968 Ericson .............................. 604/129

Primary Examiner—C. Fred Rosenbaum
Attorney, Agent, or Firm—Holman & Stern

[57] ABSTRACT

The present invention discloses an improved suction device and a method of making the same. The improved device comprises a valve means for one time use, particularly in health care field. The valve device is made from two parts which are pushed into one another while bending at least one resilient lip into a shunt conduit or into abutment over the shunt conduit opening to the channel, so that the lip is limited in its movement by another part of the device.

7 Claims, 15 Drawing Figures

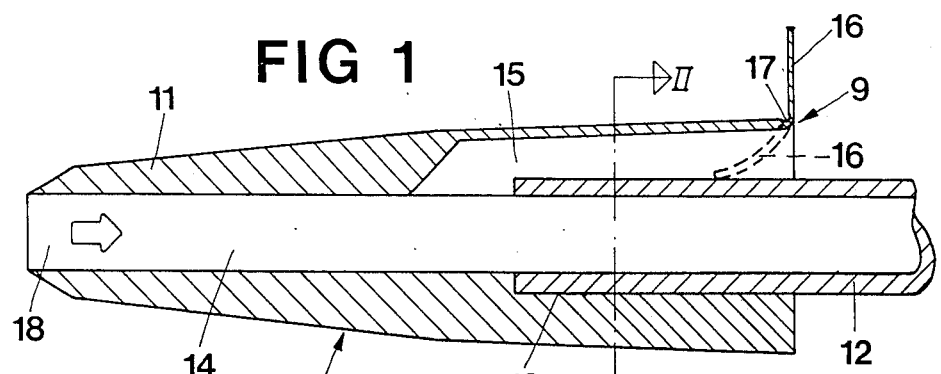
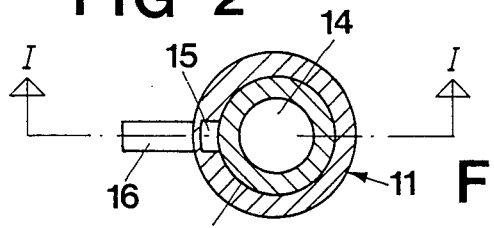
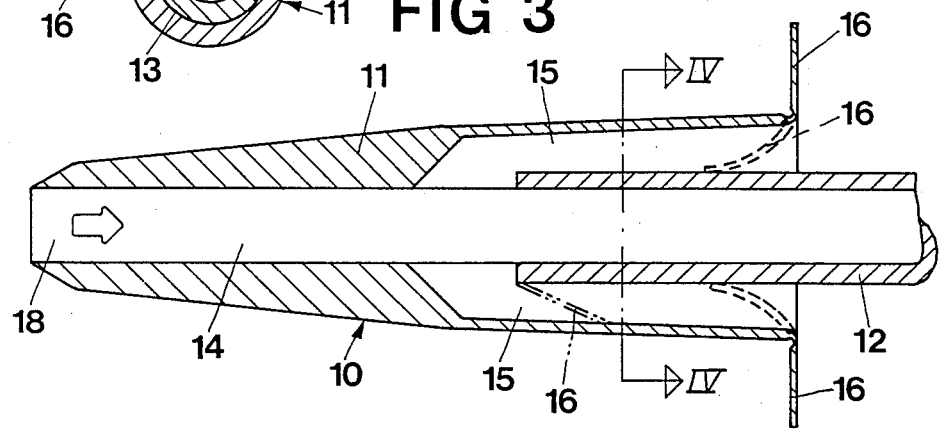
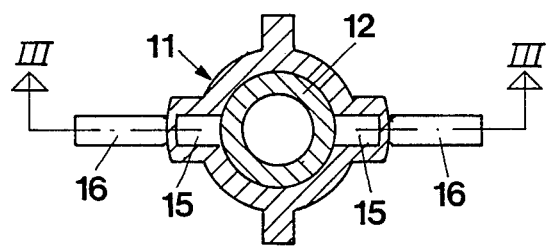

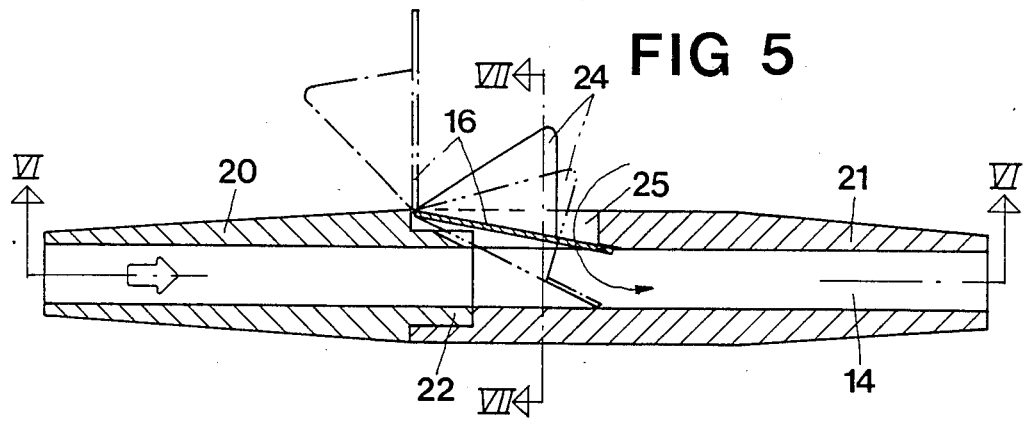
FIG 5
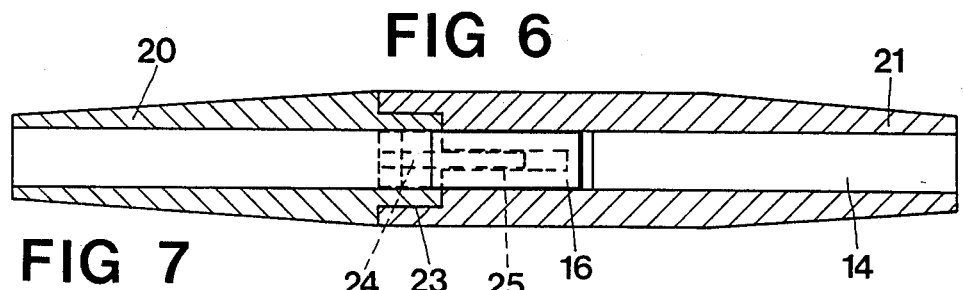
FIG 6
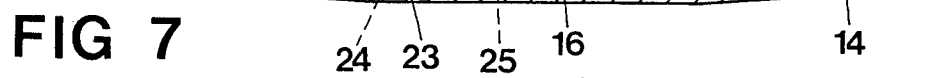
FIG 7
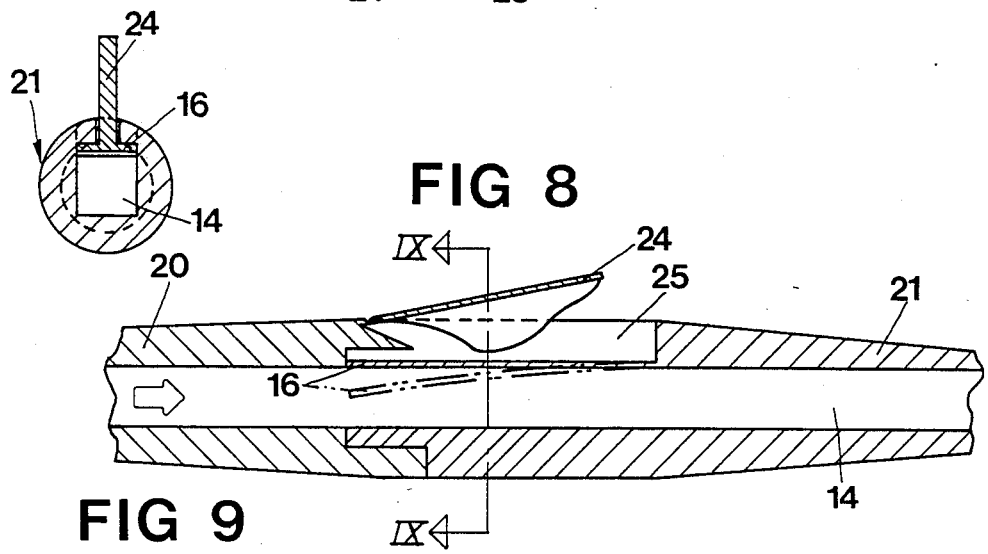
FIG 8
FIG 9
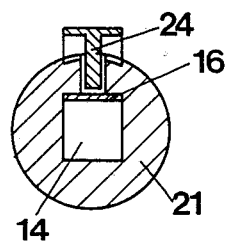

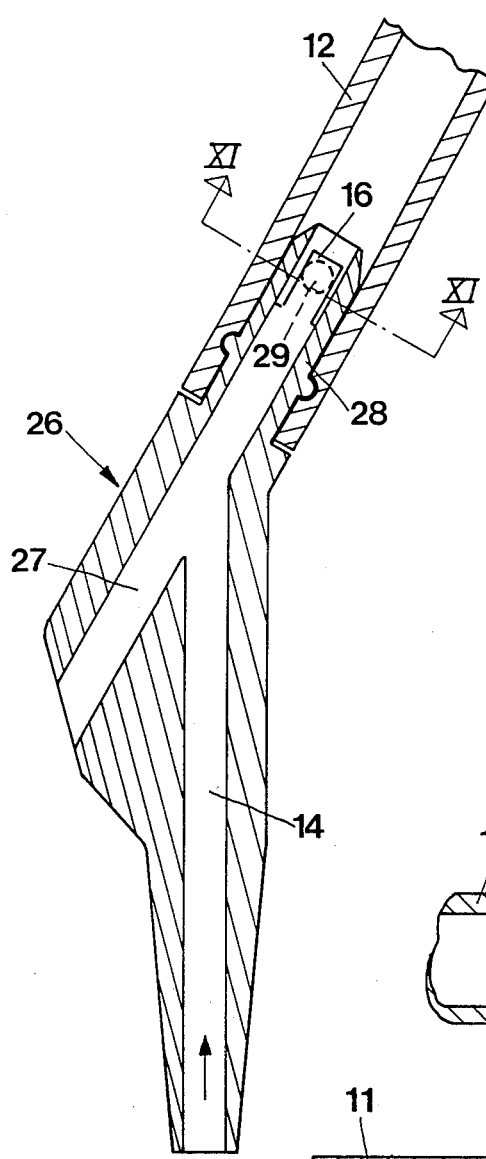
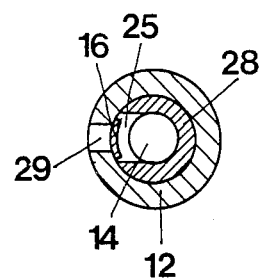
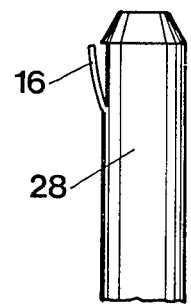
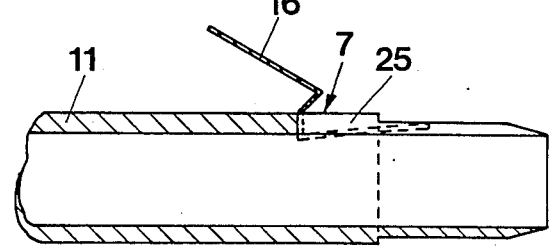
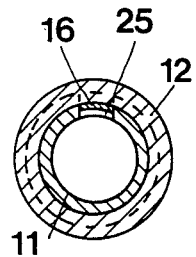
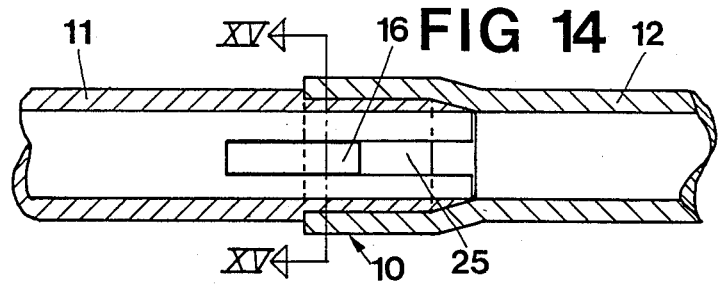

SUCTION DEVICE AND A METHOD OF MANUFACTURING THE SAME

CROSS REFERENCE TO RELATED APPLICATION(S)

This U.S. application stems from PCT International Application No. PCT/SE83/00061 filed Feb. 23, 1983.

BACKGROUND OF THE INVENTION

TECHNICAL FIELD

The present invention is related to improvement in a suction instrument or the like for one-time use in health care and of the kind comprising a valve for connecting to the suction conduit of the instrument a shunt conduit, communicating with the atmosphere.

STATE OF THE ART

Suction devices of various kind connected to a vacuum pump are used, for instance, in surgery and dental care. One problem arising in this connection is that the nozzle opening may touch body tissues so that these will adhere to the nozzle by suction. Since the vacuum pump continues to evacuate air out of the suction conduit, the pressure will be further reduced and the nozzle will adhere even more firmly. The result will be that tissues may be damaged and the nozzle opening may be blocked by loose objects. This problem may be solved in various ways. One way is to provide the suction conduit with a valve which, when the pressure difference between the atmosphere and the suction conduit exeeds a certain value, will open a flow connection between the suction conduit and the atmosphere. In this manner, the pressure in the suction conduit may never reach below this value, so that the risk of the nozzle adhering by suction will be considerably reduced. Devices of this type are previously known, but these consist of comparatively complicated mechanical devices with a valve member, a valve seat and spring, and are not suited for one-time use, and they are furthermore comparatively complicated to sterilize, since they have to be dismounted, which is a time consuming procedure. Furthermore, it is not always desirable that the valve opens at a certain pre-adjusted subpressure, such as when it is desired to suck up and remove an object.

SUMMARY OF THE INVENTION

It is, therefore, an object of the present invention to provide a simple and inexpensive device which, when in use, will not adhere by suction, or the suction power may be manually controlled in a simple way.

Another object is that the device shall be capable of being manufactured at such a low cost that it can be thrown away after use and may, therefore, consist of only a few parts.

A further object is that the mounting should be simple and, if mounting is necessary, this may be made by machine.

These objects have been attained by a device which comprises at least two parts interconnectable by means of an overlap connection or the like, one of said parts being provided at its end portion with at least one resilient lip projecting from the part, said lip being secured by the other part, after the parts have been interconnected, in a position in which it is situated in the shunt conduit or in abutment with the shunt conduit opening, the lip being adapted to block the passage through the shunt conduit in one direction.

BRIEF DESCRIPTION OF THE DRAWINGS

FIG. 1 is a section along the line I—I in FIG. 2 through the device according to the invention adapted for a connection means for a surgical suction device.

FIG. 2 is a section along the line II—II in FIG. 1.

FIG. 3 is a section analogous to FIG. 1 through a modified embodiment.

FIG. 4 is a section along the line IV—IV in FIG. 3.

FIG. 5 is a longitudinal section through a valve device according to another embodiment and adapted for a connection piece.

FIG. 6 is a section along the line VI—VI in FIG. 5.

FIG. 7 is a section along the line VII—VII in FIG. 5.

FIG. 8 illustrates a fourth embodiment of the invention in section.

FIG. 9 is a section along the line IX—IX in FIG. 8.

FIG. 10 is a section through a suction nozzle according to a further embodiment.

FIG. 11 is a section along the line XI—XI in FIG. 10.

FIG. 12 is a side view of the rear end of the suction nozzle.

FIG. 13 shows the suction hose 12 provided with a lip 16 flanged at an angle smaller than 90° in order to provide a desired spring force when bent into the open groove 25 (the position being shown with dashed lines).

FIG. 14 shows the embodiment of FIG. 13 when the valve is connected to the connection means 11; and FIG. 15 is a section along the line XV—XV in FIG. 14.

DESCRIPTION OF PREFERRED EMBODIMENTS

FIG. 1 illustrates a device 10 for a surgical suction instrument comprising two parts, one of which consists of a connection means 11 or a nipple, and the other consists of a suction hose 12 or a tube. The connection means 11 is conical and intended to be connected with some other part, i.e. a conical connection piece for another suction hose (not shown), a catheter, a broncoscopi suction device, a nozzle, etc. The device is provided with a valve which opens automatically at a certain subpressure. In this embodiment the valve 9 consists of a integrated part of the sleeve-shaped connection means 11 which is provided at its rear end, with a circular enlargement for receiving the suction hose 12. Parallel to the inner suction channel of the connection means there is provided, in said means, a groove 15 which is open towards the suction channel 14 and which is partially limited inwardly by the front end of the suction hose 12.

The connection means 11 is preferably manufactured from a thermoplastic material (PVC) by injection moulding, where, at the same time, at its rear end opposite to the groove 15 there is formed a lip 16 which connects to the connection means by means of a portion 17 of thinner material. The lip 16 is formed with a slightly smaller width than the groove 15 and with a length exceeding the depth of the groove. When the device is mounted, i.e. when the connection means is connected to the hose 12, the lip 16 is bent into the groove as illustrated in broken lines in FIG. 1, whereafter the hose 12 is inserted into the enlargement 13, the lip 16 is secured in its folded in position. The connection means 11 is secured to the hose 12, preferably by gluing.

If the front opening 18 of the connection means 11 should be plugged up and the subpressure in the hose and the connection means increases above a certain valve, the lip 16 will likewise be actuated by the suction, so that it will be lifted from its cealing position against the hose 12 and will allow passage of ambient air, thereby the suction power at the front opening will decrease or completely disappear in such a way that the object which is adhered by suction is released.

The device shown in FIGS. 3 and 4 distinguish from the device shown in FIGS. 1 and 2 by that the groove 15 and the lip 16 are doubled. This design is appropriate when relatively large suction levels and a high rate of flow is involved.

It is also possible to design the lip 16 at the hose 12, as is shown by dash-and-dott lines in FIG. 3 and directed to the one or the other direction, depending on what effect is desired. In the shown embodiment the lip 16 is turned in the opposite direction of the lip 16, in such a way that a by-pass valve function is obtained, independent of how the connection means is connected to the suction device.

At the embodiment according to FIGS. 5 and 6 the device has been applied at a loose connection part to make it possible to connect two hoses to each other. The device consists of two parts 20 and 21 designed with a thrust collar and corresponding aperture 23 for connection to each other. At one end of the part 20 a lip 16 is designed, which forms a unit together with the part 20. At the upper side of the lip there is formed an actuating part 24 formed in such a way that the lip and said actuating part together have a T-shaped cross section.

The other part 21 is provided, at the end thereof, which is connectable to the part 20, with an axial groove 25 which is slightly wider than the thickness of the actuating part 24 but smaller than the width of the lip 16. At the interconnection of the parts 20 and 21 the lip 16 will be pressed into the suction channel 14 in the other part 21, said suction channel having a rectangular cross section, where the parts are interconnected, for instance by being glued to one another.

By pushing the actuating part 24 inwardly the connection channel 25 will be opened, while at the same time the suction channel 24 will be more or less restricted.

In the embodiment according to FIGS. 8 and 9, the lip 16 is provided on the part 21, whereas the actuating member 24 is provided on the part 20. The valve device operates in the same manner as illustrated in FIGS. 5 and 6, i.e. the lip 16 seals against the groove 25 and may be made to open by the aid of the member 24.

The embodiment according to FIGS. 10–12 is a two-part device comprising a nozzle 26 and a suction hose 12. The nozzle is made for intermittent suction, i.e. it is provided with a connection channel 27 intended to be closed by a finger when suction is desired. In order to prevent the nozzle to adhere by suction to an object there is provided, in the portion 28 of the nozzle, a lip 16, which, at the manufacturing of the nozzle 26, is in the position illustrated in FIG. 12, i.e. the lip 16 is provided at the portion 28 in a position slightly projecting therefrom. When the parts are interconnected said lip is intended to lay against the inner side of the hose 12 with a certain spring pressure. Opposite to the lip 16 there is provided, in the hose 12, an opening 29 which will be uncovered when the pressure in the hose reaches a value large enough for the lip to be sucked radially inwardly against the spring-action thereof.

The invention is not limited to the embodiments shown and described but may be subject to various modifications within the scope of the claims.

I claim:

1. A valve device for use in surgical suction instruments for one-time use comprising a suction channel which passes through the device and a shunt conduit which communicates the suction channel with the exterior of the device, the device being formed by at least two parts which are connected together by means of an overlap connection with one of the parts being provided on an end portion with at least one resilient lip means projecting therefrom and connected to said one part by a portion of thinner material forming a hinge, said lip means being limited in its movement by the other part, such that it is in the shunt and in an abutting position across the shunt conduit opening to the suction channel, the lip means being adapted to block the passage of air in the direction from the suction channel to the exterior and opening when the suction channel is blocked.

2. The device of claim 1, wherein the lip means has lesser thickness than the rest of the device.

3. The device of claim 2, wherein the lip means is provided with an actuating part arranged transversely to the lip and extending through the shunt conduit.

4. The device of claim 3, wherein the free end and the side edges of the lip means are formed after the inner contour of the suction channel of the respective part and adapted to seal against the same.

5. A method of manufacturing the device as defined in claim 1 for suction instruments for one-time use, comprising making the valve device from two parts which are pushed into one another while bending at least one resilient lip means into a shunt conduit in an abutting position across the shunt conduit opening to the channel, so that said lip means is limited in its movement by another part of the device.

6. The valve device of claim 1 wherein the lip means is across the shunt conduit in an overlapping position.

7. The method of claim 5 wherein the lip means is bent across the shunt conduit in an overlapping position.

* * * * *